United States Patent [19]

Dickmann et al.

[11] 4,286,890

[45] Sep. 1, 1981

[54] GEL OR WAXY ARTICLES

[75] Inventors: Heinz H. Dickmann, Bühl; Dieter Hechenberger, Sinsheim-Eschelbach; Richard Krattner, Bühl-Neusatz, all of Fed. Rep. of Germany

[73] Assignee: Lingner & Fischer GmbH, Fed. Rep. of Germany

[21] Appl. No.: 965,693

[22] Filed: Dec. 1, 1978

Related U.S. Application Data

[63] Continuation of Ser. No. 716,875, Aug. 23, 1976, abandoned.

[30] Foreign Application Priority Data

Aug. 15, 1975 [GB] United Kingdom ............... 33997/75

[51] Int. Cl.$^3$ ............................................. B43K 27/02
[52] U.S. Cl. .................................................. 401/19
[58] Field of Search ....................... 401/16, 17, 19–20, 401/49, 88, 52, 132, 136; 428/413; 427/11, 301, 302; 118/76; 106/19, 31–32; 252/315–316; 260/26, 27 R

[56] References Cited

U.S. PATENT DOCUMENTS

| | | | |
|---|---|---|---|
| 2,409,000 | 10/1946 | Rubenstein | 401/49 |
| 3,218,273 | 11/1965 | Montesano | 428/413 |
| 3,472,675 | 10/1969 | Gordon et al. | 401/132 |
| 3,539,481 | 11/1970 | Parker | 260/27 R |
| 4,066,600 | 1/1978 | Pletcher et al. | 106/19 |

FOREIGN PATENT DOCUMENTS

| | | | |
|---|---|---|---|
| 521507 | 3/1955 | Italy | 401/49 |
| 1072272 | 6/1967 | United Kingdom . | |
| 1277425 | 6/1972 | United Kingdom . | |

*Primary Examiner*—C. Fred Rosenbaum
*Attorney, Agent, or Firm*—Jacobs & Jacobs

[57] ABSTRACT

A shaped article is produced which comprises a composite solid gel or waxy mass composed of a plurality of discrete solid gel or waxy regions having a common interface, each said region containing at least one reactive substance, the regions being so located in the shaped article that each region may be brought in contact with the desired substrate on which the reactants may be brought together and whereupon a reaction takes place.

4 Claims, No Drawings

GEL OR WAXY ARTICLES

This is a continuation of Ser. No. 716,875, filed Aug. 23, 1976 and now abandoned.

This invention relates to shaped articles comprising a composite gel or waxy mass containing two or more substances which chemically interact when mixed, to produce a desired effect or substance. These substances are in an unreactive condition in the gel mass but when the article is used, the desired substance or effect is produced.

According to the present invention there is provided a shaped article comprising a composite solid gel or waxy mass containing two or more substances which chemically interact when mixed, said composite mass being composed of discrete solid gel or waxy regions, said substances being individually or in mutually unreactive groups dissolved or dispersed in different compatible gel or waxy regions, said gel or waxy regions being so located in the shaped article that each region containing one or a group of said substances may be brought into contact with a work surface or workpiece.

The article of this invention permits two or more mutually reactive substances or mutually reactive groups of substances to be packaged together in a single article but to be kept apart (and hence in an unreacted condition) until such time as the reaction is required. At the required time, the substances or groups of substances can be mixed and allowed to react on the work surface or workpiece by applying the gel or waxy regions containing the substances or groups of substances either simultaneously or consecutively, depending on the configuration of the article.

The surprising feature of the invention is the absence of reaction between the substance or groups of substances in spite of their combined presence in the composite solid gel or waxy mass of the article. There appears to be substantially no diffusion of the reactants from their separate gel or waxy regions through the composite mass. Hence it is only when separate gel or waxy regions containing the reactants are mechanically mixed in use that reaction takes place.

Many shapes can be envisaged for articles in accordance with the invention. In one of its simplest forms, appropriate where only two mutually reactive substances are involved, an article would comprise a composite solid gel or waxy mass, in the form of a stick or crayon, composed of two discrete solid gel or waxy regions having a common interface, each containing one of the reactive substances. Such a common interface could be across the width of the crayon or stick (so that one gel or waxy region might be applied first and then by inverting the crayon or stick the second gel or waxy region might be applied) or, preferably through the length of the stick or crayon (so that both gel or waxy regions extend side-by-side along the length of the stick and both can be applied simultaneously by rubbing the tip of the stick or crayon on the work surface or workpiece). Alternatively, one of the gel or waxy regions might extend through the length of the first waxy region as a core so that again, both regions would be applied simultaneously.

A stick or crayon configuration might also be appropriate where three or more mutually reactive compounds or groups of compounds were involved. In such a case the composite solid gel or waxy mass would comprise an appropriate number of gel or waxy regions arranged with interfaces between adjacent regions running the length of the stick (e.g. side-by-side around the longitudinal axis or as a plurality of cores through a single gel or waxy region). Such a stick would, in cross-section, expose all the gel or waxy regions containing the reactants, which could consequently be simultaneously applied to the work surface or work piece.

As examples of alternative shapes for articles of the present invention may be mentioned those wherein the composite solid gel or waxy mass is shaped like a bar of toilet soap, for rubbing onto large areas of work surface, or like a small cube, sphere or lozenge which can be distorted by pressure of the fingers or by some mechanical implement to mix the discrete solid gel or waxy regions.

It will be apparent that the shape of an article in accordance with this invention will be dictated by the use to which it is to be put. It will also be apparent that in many cases, an article in accordance with the invention will include a holder or dispenser for the solid composite gel or waxy mass, such as a screw-up lipstick-type dispenser for sticks or crayons, or a handle for attachment to a soap-bar-type gel or waxy mass.

It is necessary, for this invention to be put into practice, that the gel or waxy regions containing the various mutually reactive ingredients should be compatible with these reactive ingredients. Thus, the gelling agent or wax should not inactivate, or be inactivated by, the reactive compound during work up or storage. Subject to this requirement, examples of classes of mutually reactive substances which might be included in an article according to this invention include:

(i) Polymerisable or co-polymerisable monomer systems
(ii) Curable resin systems
(iii) Effervescent or foamable systems
(iv) Endothermic or Exothermic reactive systems
(v) Dye or bleach systems Within each of the above groups, many specific examples of reactive combinations will be apparent, and the use to which articles in accordance with this invention are put will depend on the reactive combination employed.

Thus, within class (i) above, the reactive system might be an acrylic acid/initiator polymerisation system or an acrylic/methacrylic acid/initiator copolymerisation system, or a styrene/initiator polymerisation system. These are only examples of the many polymerisable monomer systems which might be used in an article intended for use as an adhesive, lacquering, or coating stick or crayon.

Within class (ii) above, the reactive system might be an epoxy resin/amino or polyamino-amide curing combination, or an epoxy resin/polymercapto ether curing combinations. Such curable resin combinations, e.g. those based on bisphenol A and a polyamino-amide or polymercapto ether are well known. Another curing system is the polyurethane/isocyanate combination.

Articles including curing resins might be in the shape of sticks used as fissure sealants or as adhesives or coating sticks. If shaped as small malleable units such as cubes or spheres, the articles might be used as plugs for fissures in e.g. masonry or automobiles.

Within class (iii) above, the use of an effervescent or foaming couple might permit the production of articles for use e.g. as edible substances such as effervescent ice lollipops or sherbert sticks and as foaming carpet shampoos or suede cleaners or as shaving soaps which foam on the face, or as pharmaceutical products such as foaming contraceptive pessaries or foaming suppositories.

Within class (iv) above endothermic or exothermic oxidation/reduction; acid/base neutralisation or hydration systems may permit the preparation of articles for use as e.g. endothermic deodorants or antiperspirants, exothermic shaving sticks, and exothermic depilatories.

Within class (v) above oxidative dye or bleaching systems will allow the preparation of sticks for colouring the hair in a particularly convenient manner, as well as novelty "magic" coloured crayons as toys for children.

It will be seen that in many of the suggested applications above, the article will include other functional ingredients other than the specific mutually reactive substances, provided they too are compatible with the gel or waxy matrix.

These "inert" functional ingredients may be included, for example, in the composite gel or waxy mass either in the discrete gel or waxy regions containing the isolated reactive ingredients or alternatively in their own discrete gel or waxy masses, providing they are positioned so that they too can be applied to the work surface or work piece.

It will be clear that since the articles of the invention are intended to enable the substances in the discrete gel or waxy regions to be mixed on a substrate during use, the gel or wax must be one which is readily transferred from the article to the substrate, not a totally rigid and intractable gel or wax.

It will also be understood that whether the composite mass which forms part of the article of this invention is a composite gel or waxy mass (or indeed a composite of discrete gel and waxy regions) will be dictated by the nature of the substances to be included in the article. Thus, some substances will be organic liquids normally, e.g. some polymerisable monomer systems, and curable resin systems. Such systems will normally be gelled using a known gelling agent such as described in German OLS No. 2204482 (a reaction product of sorbitol and benzaldehyde) or a salt of a compound of formula:

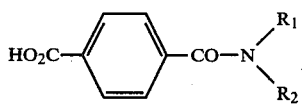

(wherein $R_1$ is hydrogen or a $C_{1-8}$ alkyl group and $R_2$ is a $C_{1-18}$ hydrocarbon group), or indeed an alkali metal salt of a fatty acid used as a gelling agent in the manner described in, for example, British patent 1230884. On the other hand, where the reactive system is a water-soluble inorganic system, gelling agents appropriate to aqueous solutions will be preferred, for example, alkali metal salts of fatty acids, salts of compounds of the formula given above, and inorganic gelling agents.

If the reactive system is a minor component of the total article, it may be preferable to use waxy materials as the basis for the composite mass of the article. Such waxes are well known and include both natural and synthetic waxes, as well as the wax acids and esters such as are described as structuring agents for adhesive sticks in, for example, British Pat. No. 1365147.

It will be clear that the choice of gelling or waxy agent which is used in the manufacture of articles in accordance with this invention is very much an ad hoc matter. However, it is within the routine skill of the worker in the art to test various gellants and waxes to find any which may be suitable. It is, of course, impossible to guarantee that in every case suitable gellants or waxes will be available.

The manufacture of articles in accordance with the invention is likewise an ad hoc matter but will present little or no difficulty once a decision has been made on the desired gellant or wax and on the final shape of the composite gel or waxy mass and the configuration of the discrete gel or waxy regions which make it up. In the case of stick or crayon articles, the use of hot melt casting procedures or of multichannel injection nozzles might be appropriate.

The invention will now be illustrated in the following nonlimiting Examples:

EXAMPLE 1

A mix of 95% by weight of an epoxy resin based on bisphenol A (Araldite M) and 5% by weight of a gelling agent which is the reaction product of sorbitol and benzaldehyde (Gel-All) was produced by heating to about 100° C. and stirring. While still hot this mix was poured into a small cylindrical mould until the mould was half-full and the mould was capped and laid on its side until the mix had cooled and gelled.

A mix of 93% by weight of a polyamino amide (Versamide) and 7% by weight of Gel-All was produced by heating to about 100° C. and stirring. This mix was then poured into the cylindrical mould containing the gelled material of the first mix, and then allowed to cool. This of course produces a solid composite gel mass resembling a crayon and composed of two longitudinal side-by-side discrete gel halves. In cross-section the stick looks like this: ⌀. where the shading simply implies different reactive ingredients.

This stick was rubbed on various substrates, such as wood, paper, metal, masonry and glass and was found to leave behind a film which cured over the normal time for such curing systems to give a hard tough resin film. There was no evidence of curing at the interface in the stick itself.

EXAMPLE 2

A mix of 95% by weight of an epoxy resin based on bisphenol A ("Empicote 828") and 5% by weight of a gelling agent which is the reaction product of sorbitol and benzaldehyde ("Gell-All") was produced by heating to about 100° C. with stirring. The hot mix was cast into cylindrical crayon moulds and pins of half the diameter of the moulds were centred in the mixes. After the mixes had cooled the pins were extracted, leaving a hollow bore along the longitudinal axis of the cooled mass.

A mix of 93% by weight of polymercapto ether (Dion Polymercaptan DPM 3-800 LC, Diamond Chemicals, Cleveland, Ohio, United States) and 7% by weight of Gel-All was produced by heating to about 100° C. with stirring. This mix was then poured into the cylindrical hollow bores of the first mixes and allowed to cool. By this procedure, crayons having an outer sheath of the first mix and an inner core of the second mix were produced. The outer sheath and inner core were of equal volumes.

This design of crayon has the advantage compared with the crayon of Example 1 that both components will be rubbed off in the same quantity, whether the stick is held vertically or diagonally.

What we claim is:

1. A shaped solid article for the application to a work surface of a reactive mixture of a curable epoxy resin and curing agent therefor, said article having a configuration about a central axis adapted for hand application and consisting of two discrete contiguous zones, the interface of said zones being aligned coaxially with said central axis, a first of said zones consisting of a solid gel or waxy mass with said curable epoxy resin dispersed therein and the second of said zones consisting of a solid gel or waxy mass with said curing agent dispersed therein, said epoxy resin and said curing agent being held in non-reactive relationship by said gels or waxy masses until mixed upon simultaneous or consecutive frictional transfer of both of said gels or waxy masses from said article to a common area of a work surface.

2. An article according to claim 1 wherein one of said zones extends as a core through the other of said zones.

3. An article according to claim 1 wherein each of said zones extend side by side along the length of said article.

4. An article according to claim 1 wherein said curing agent is an aminoamide, a polyaminoamide or a polymercapto ether.